United States Patent [19]

Sadohara

[11] Patent Number: 4,608,017
[45] Date of Patent: Aug. 26, 1986

[54] ENDODONTIC IRRIGATING INSTRUMENT
[75] Inventor: Tsuyoshi Sadohara, Yokohama, Japan
[73] Assignee: Micron Co., Ltd., Tokyo, Japan
[21] Appl. No.: 610,687
[22] Filed: May 16, 1984
[30] Foreign Application Priority Data May 20, 1983 [JP] Japan ................................. 58-88951
Aug. 1, 1983 [JP] Japan ................................. 58-140932

[51] Int. Cl.$^4$ ............................................. A61C 5/02
[52] U.S. Cl. .................................................... 433/81
[58] Field of Search ........................... 433/81, 91, 118

[56] References Cited

U.S. PATENT DOCUMENTS

| 1,987,907 | 1/1935 | Jenkins . | |
|---|---|---|---|
| 2,449,497 | 9/1948 | McLeod . | |
| 3,164,153 | 1/1965 | Zorzi | 433/91 |
| 3,256,885 | 6/1966 | Higgins et al. | 433/91 |
| 3,807,048 | 4/1974 | Malmin . | |
| 4,217,101 | 8/1980 | Loge | 433/126 |

FOREIGN PATENT DOCUMENTS

| 673696 | 3/1939 | Fed. Rep. of Germany . |
|---|---|---|
| 3026929 | 7/1980 | Fed. Rep. of Germany . |
| 1334134 | 9/1962 | France . |
| 2234884 | 6/1974 | France . |
| 256175 | 2/1949 | Switzerland . |

OTHER PUBLICATIONS

European Search Report.

Primary Examiner—Robert Peshock
Attorney, Agent, or Firm—Merchant, Gould, Smith, Edell, Welter & Schmidt

[57] ABSTRACT

An endodontic irrigating instrument comprises a handpiece having an internal liquid passage therethrough extending from a liquid inlet formed in the proximal end of the handpiece to a liquid ejection nozzle provided at the distal end. The handpiece incorporates a suction or vacuum pump of the airjet or ejector type which comprises an air nozzle connected by a passage with an air inlet formed also in the proximal end of the handpiece. The vacuum chamber of the suction pump is connected by a separate internal passage in the handpiece with an aspiration needle provided adjacent to the liquid ejection nozzle. The proximal end of the handpiece is designed to be fitted with a coupling joint attached to a multiple-channel flexible hose which is conventionally used to supply compressed air and pressurized water from a dental unit to conventional air-driven dental turbine tools. Thus, the endodontic irrigating instrument can be used interchangeably with existing turbine tools.

12 Claims, 9 Drawing Figures

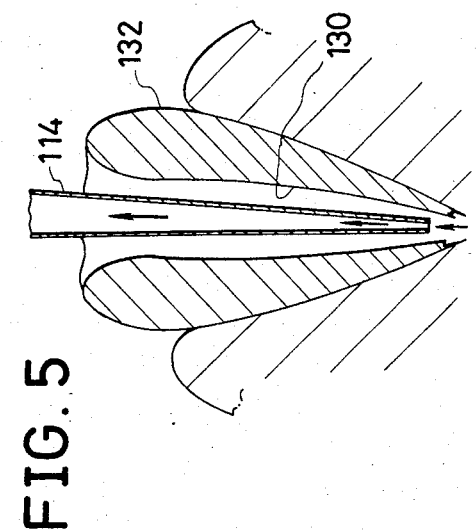
FIG. 5
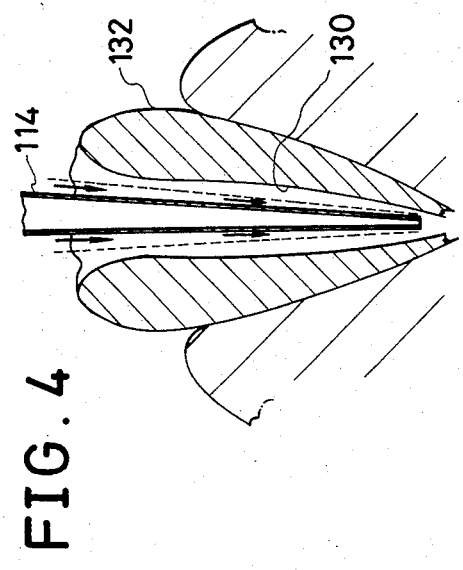
FIG. 4
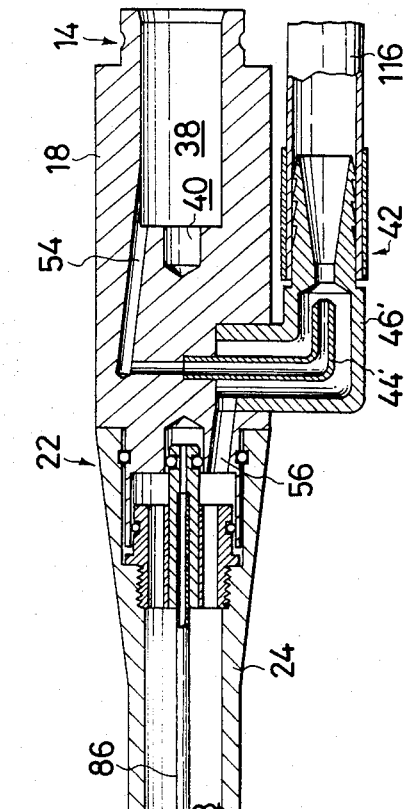
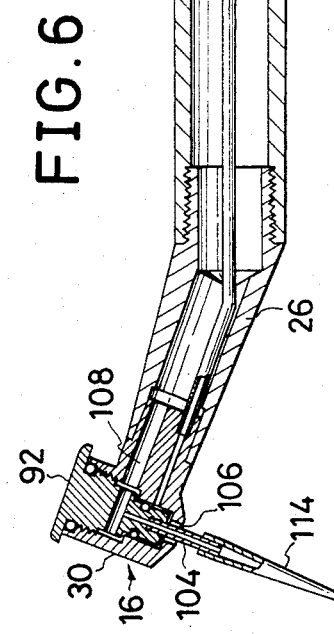
FIG. 6

ENDODONTIC IRRIGATING INSTRUMENT

BACKGROUND OF THE INVENTION

(1) Field of the Invention

The present invention relates to an instrument for use in dental surgery and, more particularly, to an endodontic instrument for irrigating the root canal of a tooth with an irrigating liquid.

(2) Description of the Prior Art

In root canal treatment such as pulpectomy and root canal apical seat preparation, it is essential that the cuttings and dental pulp tissue fragments resulting from reaming by reamer files be completely removed from the root canal, by washing, and the inside of the root canal be perfectly disinfected and dried prior to filling. Also, an open end root canal containing food stuff residuals must be irrigated before each treatment.

Of the known endodontic irrigating instruments, there is a minium syringe by which irrigating solutions such as a hydrogen peroxide solution and sodium hypochlorite solution are alternately injected into the root canal. One of the disadvantages of the minium syringe is that the volumetric capacity is limited, and the irrigating solutions must be often replenished. Another disadvantage is that if the irrigating needle of the minium syringe is inserted too deeply into the root canal or the pressure of the irrigating solutions is augmented to enhance the irrigating effect, there is a danger that the irrigating solution will flow through the apical dental foramen into the periapical area, thereby breaking the periapical tissue or, in some cases, causing the formation of pneumatosis. A further disadvantage of the minium syringe is that a suction tube of a saliva remover must be inserted into or hang from the mouth to extract the used irrigating solutions. This hinders the work of the dentist and gives discomfort or pain to the patient.

Another irrigating instrument known in the art is the so-called "triple syringe". This instrument includes a nozzle connected by flexible hose with a source of compressed air and a source of pressurized water or solution provided in the dental unit, and is adapted to selectively eject either an airjet, a waterjet, or a mixture thereof. The triple syringe is not considered suitable for endodontic irrigation of a narrow root canal because the nozzle of the syringe is considerably larger in size than the diameter of the tooth cavity opening. This entails positioning the nozzle outside the tooth cavity and blowing the jet of air, water or mist from above the tooth cavity opening, making it practically impossible to produce a path within the root canal for the incoming jet and a counter-current path for the outgoing fluid, thus limiting the irrigating effect of the triple syringe. Another drawback of this instrument is that it is impossible to dispose of an air bubble trapped at the root canal apex region, to rinse that region. Moreover, as for the minium syringe, a saliva remover is required to remove the liquid after use from the patient mouth.

There is also known in the art an endodontic irrigating equipment which comprises a handpiece connected through a flexible multiple-channel hose with a remote main unit in which a vacuum pump is provided. The head of the handpiece comprises a suction or aspiration tube projecting therefrom and connected with the vacuum pump via a suction conduit in the handpiece and the flexible hose. A hollow irrigating needle is mounted to the handpiece head at the center of the suction tube, to project beyond the suction tube. Thus, an annular space is formed between the suction tube and the needle, to which space a partial vacuum is applied from the vacuum pump. The irrigating needle is connected through one or more liquid conduits in the handpiece and through passages in the hose with one or more reservoirs for irrigating solutions. An annular sealing rubber is attached to the end of or around the suction tube. In use, the irrigating needle is inserted into the root canal with the sealing rubber being tightly urged against the tooth, to hermetically seal the annular gap between the tooth cavity and the suction tube. Then the vacuum pump is operated to apply a partial vacuum within the tooth cavity so that the irrigating solution is injected through the irrigating needle into the bottom of the root canal under the action of the vacuum. The issued irrigating solution flows from the bottom to the top of the root canal and then into the pulp chamber and, by so doing, washes away the cuttings and rinses the internal cavity of the tooth. The used solution is sucked into the suction tube and is evacuated to a waste container provided in the main unit.

This irrigating equipment enjoys a certain advantage over the above-mentioned irrigating instruments in that the irrigating needle can be inserted deep in the root canal and that the used irrigating solution is discharged simultaneously with the rinsing operation.

However, this equipment requires a main unit provided with a vacuum pump and is used exclusively for the sole purpose of irrigation. This increases the cost of the equipment and imposes a financial burden on the dentist. Further, it is often difficult to perfectly seal the gap between the tooth and the suction tube with the sealing rubber. In the event of improper sealing, the tooth cavity will not be subjected to vacuum strong enough to suck the irrigating liquid into the cavity and to also generate the jet of irrigating solution required for washing. A further disadvantage of this irrigating equipment is that, as the opening of the tooth cavity is sealed by the sealing rubber, visual inspection by the dentist of the root canal is prohibited. Still further, it is impossible to move the irrigating needle along the root canal in an attempt to wash the various region of the canal, because the head of the handpiece is fixed by the sealing rubber. Thus, if the bottom of the root canal near the root apex is to be rinsed, the depth of the root canal must be measured beforehand by X-ray photographs and the needle must be cut to a desired length. Similarly, where upper regions of the root canal are to be irrigated, a number of needles having various lengths must be provided and successively exchanged. The use of sealing rubber causes another inconvenience. That is, as the outlet of the irrigating needle is positioned at a fixed location of the root canal and the solution is supplied only at that location, other areas of the root canal must be washed by the back flow of the solution. This resulted in a poor irrigating performance. A further drawback of this equipment is that it is incapable of removing a liquid droplet trapped by the capillary or adhesive action at the region of the root canal apex or apical foramen, because the suction takes place at the upper region of the tooth cavity where it is sealed.

SUMMARY OF THE INVENTION

It is therefore an object of the present invention to provide an endodontic irrigating instrument which functions without recourse to a separate vacuum pump containing unit and which is operated by a drive source of an existing dental unit which is standard equipment in almost all dental clinics.

Another object is to provide an endodontic irrigating instrument which is capable of being connected by a single action with an existing multiple-channel hose extending from the dental unit and used for coupling the turbine-driven dental instruments such as drilling tools, and which is readily interchangeable with such turbine-driven instruments when necessary.

A further object is to provide an endodontic irrigating instrument which may be controlled by an existing foot switch of the dental unit.

Still another object is to provide an endodontic irrigating instrument which is capable of discharging used irrigating solution simultaneously with the rinsing operation and which does not require an additional saliva remover.

A still further object is to provide an endodontic irrigating instrument which is capable of rinsing any desired location of the tooth cavity including the root canals and pulp chamber, particularly the apex region of the root canal, where an air bubble or liquid droplet tends to be trapped.

A further object is to provide an endodontic irrigating instrument which permits quick and perfect removal of used irrigating solutions from any location in the root canal and which is capable of drying the root canal to a degree sufficient for subsequent filling operation.

A further object is to provide an endodontic irrigating instrument which can obviate the danger of pneumatosis and fracture of the apical dental foramen that would otherwise be caused due to the high-pressure and high-velocity jet of irrigating solutions.

A further object is to provide an endodontic irrigating instrument which permits visual inspection of the root canal during irrigation.

A yet further object is to provide an endodontic irrigating instrument having an irrigating needle which is capable of being oriented at any desired angular position at the option of the dentist, to facilitate irrigation of any tooth at any position.

A still further object is to provide an endodontic irrigating instrument which is capable of controlling the flow rate of irrigating solutions.

Another object is to provide an endodontic irrigating instrument which is capable of backwashing the aspiration needle and suction passages when they are clogged by cuttings and the like.

An endodontic irrigating instrument according to the present invention comprises a handpiece having proximal and distal ends and an intermediate portion therebetween. An air inlet and a liquid inlet are provided at the proximal end of the handpiece to receive compressed air and an irrigating solution, respectively. The handpiece proximal end is adapted to be coupled with a multiple-channel hose extending from a dental unit. The intermediate portion is designed to be gripped by the operator. The distal end, forming the head of the handpiece, is provided with a suction tube to which is detachably mounted a hollow aspiration needle. A liquid ejection nozzle is provided at the distal end of the handpiece, adjacent to the suction tube, to supply the irrigating liquid under pressure along the aspiration needle.

The handpiece incorporates an airjet-type suction pump at the region adjacent to the proximal end of the handpiece. The pump is connected by an air passage with the air inlet and is energized by the compressed air to produce a zone of partial vacuum, which is transmitted through a suction passage in the handpiece and the suction tube to the aspiration needle.

The irrigating liquid under pressure, such as water and irrigating solution, is fed from the liquid inlet via a liquid passage in the handpiece to the ejection nozzle, flows therefrom at a controlled flow rate along and around the aspiration needle and is injected into to root canal to be irrigated.

Preferably, the aspiration needle is formed from a flexible, transparent material and is tapered toward its free end which has an outer diameter substantially smaller than the inner diameter of the root canal. The irrigating liquid after rinsing the internal wall of the root canal is sucked under the action of the vacuum into the aspiration needle and is discharged toward an exhaust port of the suction pump together with the used drive air.

This invention also features a suction tube for mounting the aspiration needle positioned at an angle with respect to the longitudinal general axis of the handpiece, to facilitate the dentist's work.

According to another feature of the invention, the handpiece comprises a first section including the proximal end and a second section including the distal end, the second section being mounted on the first section for rotation about the longitudinal general axis of the handpiece to enable the operator to direct the aspiration needle at any desired angular position.

Preferably, a flow control valve is provided in the liquid supply passage to regulate the flow rate of the irrigating liquid ejected from the nozzle.

The suction pump may be positioned transversely to the handpiece so that the exhaust port of the pump extends at a right angle to the handpiece.

In an alternative embodiment, the suction pump may be disposed parallel to the longitudinal general axis of the handpiece so that the exhaust port is directed rearward. In use, the exhaust port of the suction pump may be coupled to a flexible conduit leading to a suitable waste disposal installation, such as a spitoon provided in the dental unit.

In another embodiment, the endodontic irrigating instrument further comprises a valve mechanism for closing the exhaust port of the airjet pump and directing the compressed air to flow through the suction passage in the handpiece toward the aspiration needle, thereby permitting backwashing of the aspiration needle and suction tube.

These and other features of the present invention, as well as the advantages thereof, will become apparent when reading the following description in conjunction with the accompanying drawings.

BRIEF DESCRIPTION OF THE DRAWINGS

FIG. 4 is a schematic representation showing irrigation of a root canal using the instrument according to the present invention;

FIG. 5 is a schematic representation showing the irrigation liquid sucked into the aspiration needle;

FIG. 6 is a longitudinal vertical cross-sectional view of another embodiment of the present invention;

DETAILED DESCRIPTION OF THE PREFERRED EMBODIMENTS

Figure 1:
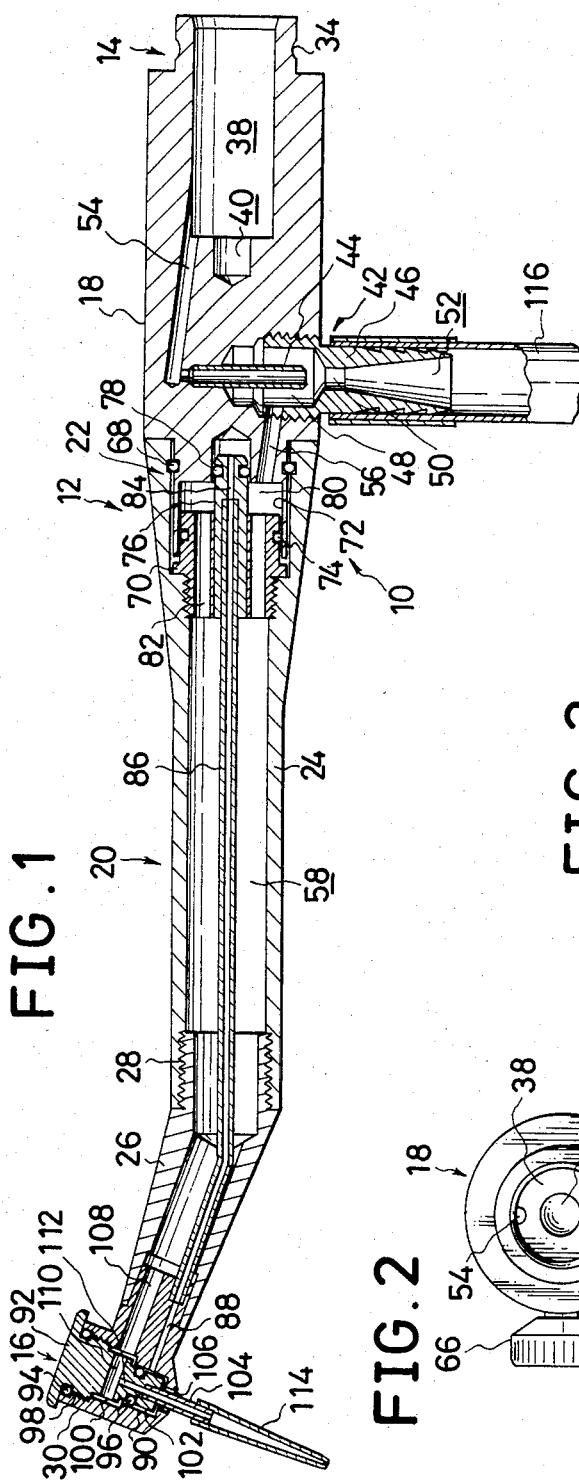
FIG. 1 is a longitudinal vertical cross-sectional view of an endodontic irrigating instrument according to the present invention.
Figure 3:
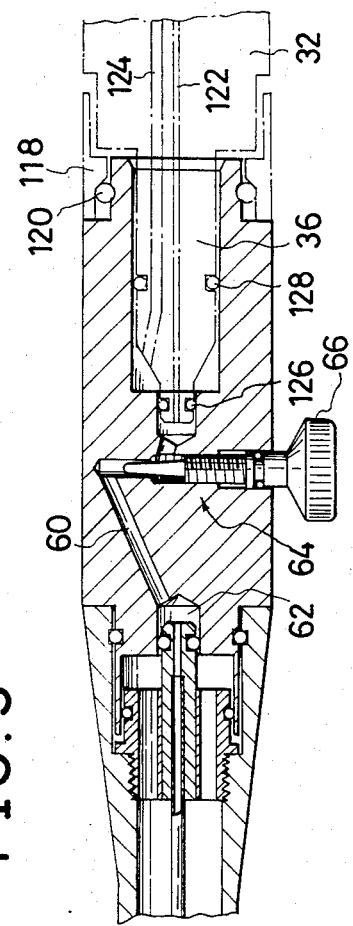
FIG. 3 is a partial horizontal cross-sectional view of the instrument shown in FIG. 1, coupled with a coupling joint.
Figure 2:
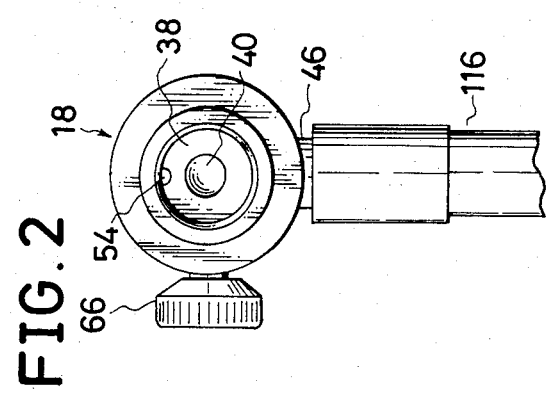
FIG. 2 is a rear end view of the instrument shown in FIG. 1.

Referring now to the drawings, FIGS. 1 through 3 illustrate a first embodiment of the present invention. The endodontic irrigating instrument, generally designated 10, comprises a handpiece 12 which extends from its proximal end 14 to its distal end 16. As seen in FIG. 1, the hand piece 12 is designed to be gripped by an operator along the intermediate portion between the proximal end 14 and distal end 16. In the illustrated embodiment, the handpiece 12 is divided into two sections, i.e., a first section 18 and a second section 20, which are coupled together to permit relative rotation by a swivel joint mechanism 22, described later. The second section 20, in turn, includes a tubular main piece 24 extending along the longitudinal general axis of the handpiece 12, a tubular intermediate piece 26 firmly joined to the main piece 24 by a threading engagement at 28, and a head piece 30 press-fitted to the intermediate piece 26. As shown, the intermediate piece 26 is slanted to raise the head piece 30 at an angle.

The first section 18 is generally cylindrical and the end 14 of the section is adapted to be coupled with a coupling joint 32, described later and shown by dotted line in FIG. 3. For this purpose, the end 14 is recessed stepwise and an annular groove 34 is formed. Also, the first section 18 has a stepped bore for receiving a core 36 of the coupling joint 32, the stepped bore serving also to form an air inlet 38 and a liquid inlet 40.

The first section 18 of the handpiece 12 is provided with a suction or vacuum pump 42 of the type known as an airjet or ejector pump. The suction pump 42 comprises an air nozzle 44 press-fitted within a radially extending stepped bore in the section 18, and a venturi tube 46 screwed partly into the radial bore. The venturi tube 46 defines therein a vacuum or suction chamber 48, a mixing chamber 50, and an exhaust port 52, which is formed in a diffuser portion of the venturi tube 46. The air nozzle 44 communicates with the air inlet 38 through an air passage 54 in the first section 18, while the suction chamber 48 is connected via a passage 56 in the first section 18 with an internal suction passage 58 formed in the second section 20. As shown in FIG. 3, the liquid inlet 40 is connected through a liquid passage 60 with an axial bore 62 formed in the first section 18 opposite the proximal end 14. A needle valve 64 having a thumbwheel 66 is provided across the liquid passage 60 to control the flow rate of the irrigating liquid.

The swivel joint mechanism 22 includes an O-ring 68 received within a pair of opposed annular grooves, one formed in the first section 18 and the other in the main piece 24 of the second section 20. The O-ring 68 permits rotation of the main piece 24 with respect to the first section 18 but serves to prevent the main piece 24 from separating from the section 18. The swivel joint mechanism 22 also includes a substantially cylindrical member 70, the externally threaded end of which is firmly screwed into the main piece 24 and the other end of which extends into a tubular extension 72 of the first section 18 and is sealed therefrom by an O-ring 74. The cylindrical member 70 has a central through-bore in which is press-fitted an integral central pipe 76 which extends into the axial bore 62 in the first section 18 and is sealed by an O-ring 78. Thus, a sealed annular space 80 is defined between the first section 18 and the main piece 24, which space 80 is communicated by the passage 56 (FIG. 1) with the suction chamber 48. The annular space 80 is then connected with the internal suction passage 58 by way of two or more axial passages 82 formed in the member 70. The central pipe 76 has a through passage 84 which opens into the bore 62.

The passage 84 in the central pipe 76 is connected by a liquid conduit 86 with a passage 88 formed in the head piece 30 and opening into the smallest bore portion of a multistage stepped bore 90 in the head piece 30. An exchangeable adapter or suction tube holder 92 with O-rings 94 and 96 is screwed into the stepped bore 90 at 98 to form sealed annular upper and lower spaces 100 and 102 between the bore 90 and the holder 92. The holder 92 firmly supports a suction tube 104 made, for example, from stainless steel, and extending outward through a nozzle 106 in the head piece 30. The upper annular space 100 is connected on one hand with the suction passage 58 via a passage 108 in the head piece 30 and on the other hand with the suction tube 104 by means of a diametrical passage 110 and a longitudinal passage 112, both formed in the holder 92.

An aspiration needle 114 is detachably mounted to the suction tube 104. The needle 114 may be made from a flexible transparent material such as polyethylene (PE) and polypropylene (PP) and is tapered toward its free end. The length of the aspiration needle 114 may generally vary from 15 to 25 mm. For the purposes of irrigating a root canal of a tooth, it is desirable that the free end of the needle 114 has an outer diameter of less than about 0.5 mm. However, the size of the needle 114 may be altered as required. Further, the needle 114 may be made from a material such as stainless steel, which is capable of withstanding inside vacuum when the wall thickness of the needle is extremely reduced. In this instance, the suction tube 104 and the aspiration needle 114 may be formed as a one-piece element.

In use, an end of an exhaust hose 116 is connected to the venturi tube 46 and the other end of the hose is led to a conventional waste liquid disposal facility such as a spitoon (not shown) normally provided in the dental unit. Then, a coupling joint 32 of a multiple-channel hose is snap fitted to the irrigating instrument 10 as shown in FIG. 3. Commercially available dental units fabricated by various manufacturers and purchased by dentists today are generally provided with a multiple-channel hose for supplying the compressed air and pressurized cooling and rinsing water to turbine-driven dental tools. The supply of air through the air channel is generally controlled by a foot pedal valve. The hose is connected to the turbine tool by a coupling joint or hose connector. Various types of coupling joints are currently used for this purpose, an example is as shown in FIG. 3. This coupling joint 32 is of the quick or one-touch coupling type and includes a slidable collar 118 for urging balls 120 radially inwardly into engagement with an annular groove of the tool, such as the annular groove 34, to perform coupling. The joint 32 has a central water supply passage 122 communicating with the water channel of the hose (not shown) and a parallel air supply passage 124 connected with the air channel. The air passage 124 opens to the side of the core 36 located between O-rings 126 and 128. If the existing dental unit is equipped with other types of coupling joints such as a screw-thread joint or bayonet joint, it is possible to couple that joint with the irrigating instrument 10 according to the present invention by an adaptor provided with the joint coupler 32, as illustrated.

When the water under pressure is fed from a remote water source in the dental unit to the water inlet 40 of the handpiece, the water flows into the passage 60 and its flow rate and the pressure are controlled manually by regulating the valve 64. The water passes the bore 62, pipe 76, liquid conduit 86, and passage 88 to flow into the annular space 102 in the head piece 30. Then the water is ejected through the nozzle 106 in the form of an annular water jet, flowing along and around the suction tube 104 and the aspiration needle 114. It is generally considered desirable to adjust the flow control valve 64 in such a manner that, when the second section 20 of the handpiece 12 is turned to direct the aspiration needle 114 upward, the water jet is ejected to a sufficient height that will carry it beyond the free end of the aspiration needle 114.

FIG. 4 schematically shows a manner in which the aspiration needle 114 is inserted into the root canal 130 of a tooth 132 and the water jet flows along the needle 114 to wash away the cuttings and pulp tissues in the root canal.

Simultaneously with the water supply, the foot pedal valve (not shown) of the dental unit is operated to supply the compressed air to the air inlet 38 of the handpiece 12. As the air is ejected from the air nozzle 44 of the suction pump 42, a partial vacuum is established within the vacuum chamber 48 and is transmitted through the passage 56, annular space 80, axial passages 82, internal suction passage 58, annular space 100, passage 110, passage 112, and suction tube 104 to the aspiration needle 114, whereby the rinsing water in the root canal 130 is sucked into the aspiration needle 114, as shown in FIG. 5, together with the cuttings and the tissue fragments and is discharged through the suction passages toward the exhaust hose 116.

Where it is desirable to perform irrigation with irrigating solutions such as peroxide solution in place of rinsing water, a sealed container receiving such a solution may be provided and pressurized by introducing the compressed air from the dental unit. The pressurized irrigating solution may then be fed by a supply conduit either to the liquid channel of the multiple-channel hose or to the liquid passage 122 of the coupling joint 32.

It will be appreciated that, according to the present invention, the irrigating solution is simultaneously extracted and evacuated by the same irrigating instrument. This eliminates the need for separate suction devices such as saliva removers and facilitates the work of the dentists. The aspiration needle 114 may be inserted at any desired depth of a root canal depending on the nature and stage of the treatment, and the transparency of the needle 114 assists in the visual inspection of the irrigating operation. The flexibility of the aspiration needle 114 enables the insertion of the needle tip within a narrow root canal of any complex structure. Thus, any portion in a root canal may be perfectly rinsed and the cuttings or other materials adhering to the root canal wall are clearly washed away. Particularly, those regions of the root canal, such as the root canal apex and apical dental foramen, that are apt to trap an air bubble and are difficult to be rinsed with the conventional irrigating instrument, can be perfectly irrigated and the irrigating solution after use may be readily removed from those regions by suction.

The irrigated root canal may be dried by using the irrigating instrument 10 of the present invention. To this end, the needle valve 64 or a foot pedal valve (not shown) for controlling the liquid supply is operated until the liquid supply is shut off. The aspiration needle 114 is moved up and down along the root canal, to discharge all droplets of irrigating solution adhering to the internal wall of the root canal. On so doing, a flow of fresh air is drafted into the root canal due to suction by the airjet pump 42. The draft of air accelerates the drying of the root canal, and the root canal is now ready for a subsequent filling operation.

It will be also appreciated that the irrigating instrument 10 according to the present invention may be used interchangeably with the dental turbine handpieces, because the suction pump 42 is operable with the compressed air. Thus, the irrigating instrument may be controlled by the conventional foot pedal valves provided in the existing dental units. As most dentists are skilled in the operation of foot-pedal controlled turbine handpieces, the irrigating instrument 10 of the present invention may be controlled without difficulty. This will enhance the efficiency of the irrigation operation. Also, the flow rate of the compressed air may be varied by regulating the foot pressure on the foot pedal, so as to control the suction force prevailing at the aspiration needle 114.

FIG. 6 illustrates a modified embodiment of the present invention. This embodiment differs from that shown in FIGS. 1 through 3 only in the direction of the suction pump. Therefore, like reference numerals are used to indicate equivalent parts and members and the description thereof will not be repeated. In this embodiment, the air nozzle 44' and the venturi tube 46' are bent rearward at a right angle so that the exhaust port is directed parallel to the longitudinal centerline of the handpiece 12. This arrangement will permit the operator to grip the handpiece 12 more conveniently.

During irrigation using the irrigating instrument 10 according to the present invention, it will happen that the narrow aspiration needle 114 or suction tube 104 becomes clogged with solid materials such as cuttings. In that event, it is desirable to backwash the needle 114 or suction tube 104 by supplying the compressed air in the reverse direction to remove the clogging materials.

Figure 7:
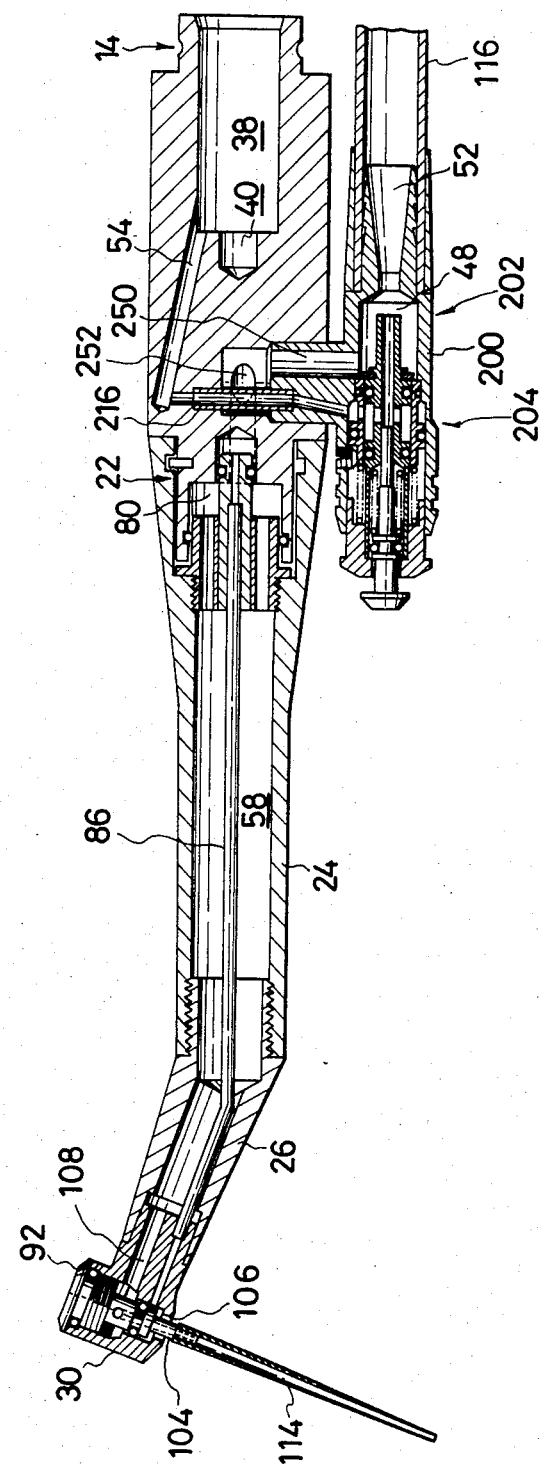
FIG. 7 is a longitudinal vertical cross-sectional view of a further embodiment of the present invention; and, FIGS. 8 and 9 are enlarged cross-sectional views showing the airjet suction pump with a built-in backwash control valve of the embodiment of FIG. 7, with FIG. 8 illustrating the pump in the operating condition and the valve in the inoperative position, and FIG. 9 illustrating the pump in the inoperative condition and the valve in the operating position.
Figure 8:
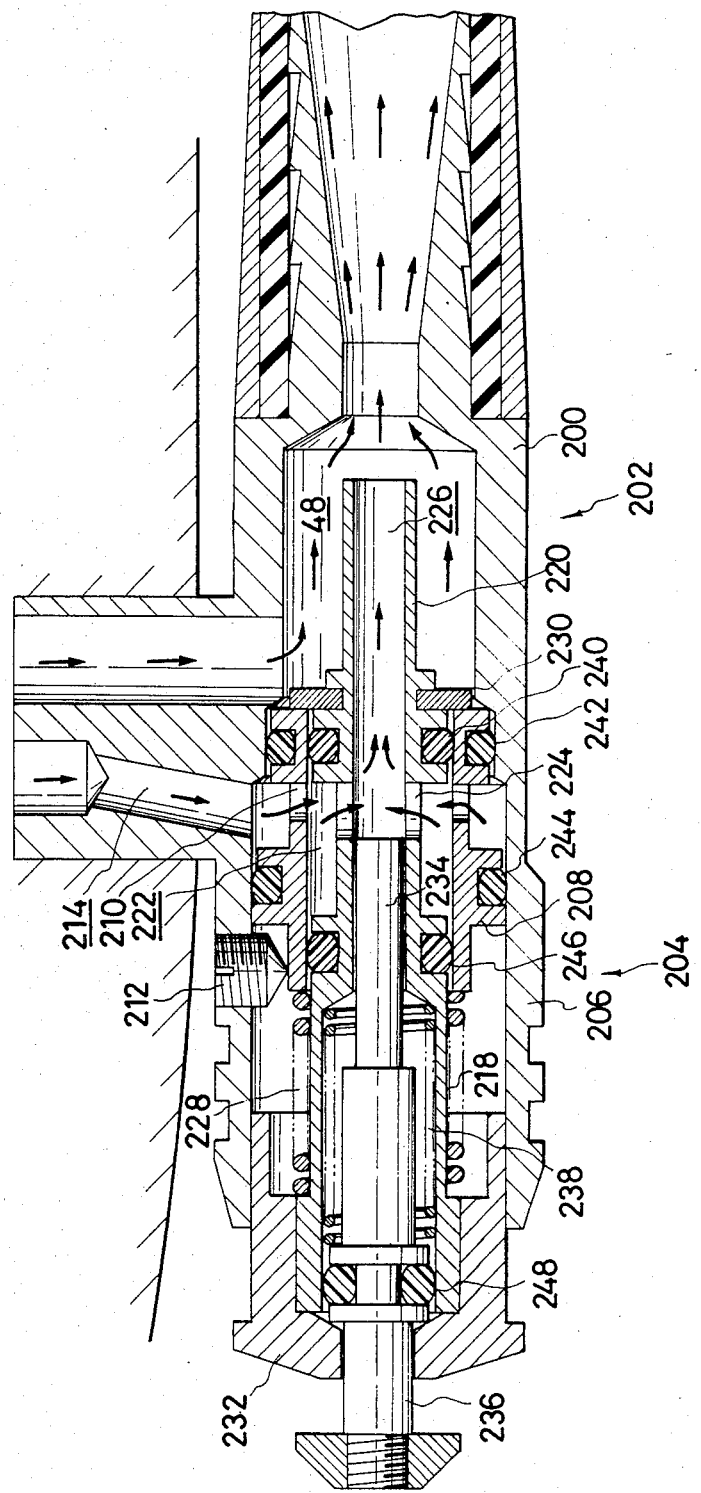
Figure 9:
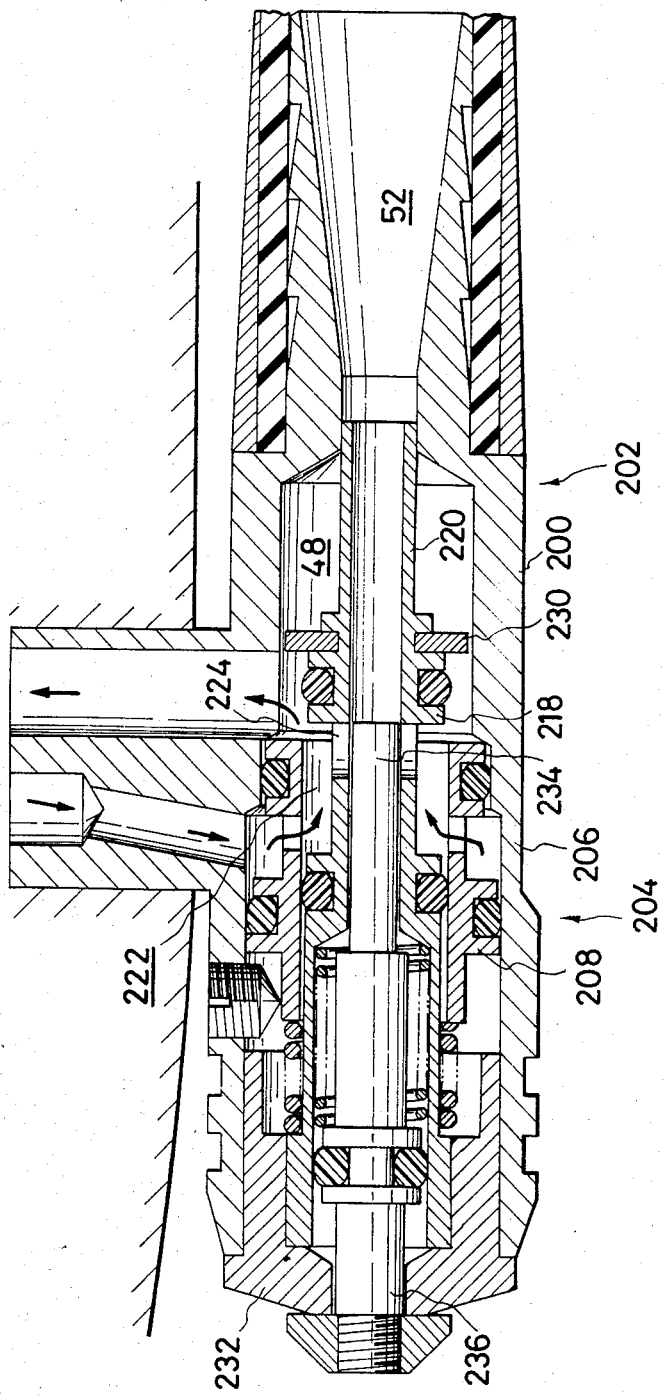

FIGS. 7 through 9 illustrate a third embodiment of the present invention which permits the above-mentioned backwashing. Parts and members equivalent to those of the preceding embodiments are designated by like reference numerals and their explanations are omitted. Only the different parts and members will be described hereinafter.

In this embodiment, the venturi tube 200 of the airjet type suction pump 202 is bent, as in the second embodiment shown in FIG. 6. As will be best understood from FIG. 8, the suction pump 202 is provided with an integral built-in valve mechanism designated generally by reference numeral 204. The valve mechanism 204 includes a valve cylinder 206 which forms an integral horizontal extension of the venturi tube 200. A stationary sleeve 208 having ports 210 is received within the valve cylinder 206 and is fixed in position by a lock screw 212. The ports 210 of the sleeve 208 are connected by a passage 214 with an air supply conduit 216 (FIG. 7) which is communicated with the air inlet 38.

A hollow movable spool 218 is slidably mounted within the fixed sleeve 208. This spool 218 is made as a one-piece member with the air nozzle 220 of the suction pump 202. The compressed air from the ports 210 is admitted into an annular space 222 around the movable spool 218 and then introduced through ports 224 into the ejection port 226 of the air nozzle 220. The movable spool 218 is urged to the left by a coil spring 228, but its leftward movement is limited by a circlip 230 mounted to the spool 218 and abutting against the stationary sleeve 208. An end cap 232 is slidably received within the valve cylinder 206 and is rigidly connected with the movable spool 218 by a suitable fastening means such as a screw thread or interference fit. A closure plunger 234 having an integral push rod 236 is mounted within the movable spool 218 and is biased toward the left by a coil spring 238. Designated at 240 through 248 are O-rings for sealing purposes. Liquid supply passages are formed in the same manner as in the first embodiment shown in FIG. 3. As is apparent from FIG. 7, the suction chamber 48 of the vacuum pump 202 is connected by passages 250 and 252 with the annular space 80.

The operation of the third embodiment provided with a backflow valve mechanism is as follows.

As each member of the valve mechanism is in the position shown in FIGS. 7 and 8, the compressed air flows as shown by arrows, and induces partial vacuum in the vacuum chamber 48 thereby causing a suction force at the aspiration needle 114.

When the aspiration needle 114 or suction tube 104 is clogged or jammed for any reason, the operator presses the push rod 236 together with the end cap 232 as shown in FIG. 9. This causes the movable spool 218 and the closure plunger 234 to move the right, whereby the annular space 222 is brought into open communication with the vacuum chamber 48 thereby releasing the compressed air toward the suction passages. At the same time, the ports 224 of the air nozzle 220 is closed by the plunger 234 and the exhaust port 52 is shut off by the frontal end of the nozzle 220. Thus, the compressed air within the chamber 48 is forced to flow into the suction passages in the reverse direction, as shown by arrows, and forced out from the suction tube 104 and aspiration needle 114, thereby blowing out the clogging materials. When the clogged materials are removed by repeating several backflow operations, the operator is then able to continue the irrigating operation.

While the present invention has been described with reference to the specific embodiments thereof, it should be understood that it is not limited thereby and various changes and modifications may be made therein within the scope of the appended claims.

I claim:

1. An endodontic irrigating instrument for irrigating a root canal of a tooth, which comprises:
    a handpiece having a proximal end and a distal end, said proximal end having an inlet for a compressed air and an inlet for an irrigating liquid under pressure and being so formed as to be coupled with a multiple-channel hose extending from a dental unit;
    a suction pump of the airjet type incorporated with said handpiece at the region adjacent said proximal end thereof, said suction pump having an air nozzle and and exhaust port;
    air passage means for supplying a flow of compressed air from said air inlet to said nozzle to create a zone of partial vacuum in said pump;
    a hollow aspiration needle mounted at an end thereof to said distal end of the handpiece, the other end thereof having an outer diameter substantially smaller than the inner diameter of the root canal to be irrigated;
    suction passage means for connecting said zone of partial vacuum with said aspiration needle to suck the irrigating liquid therein and to discharge it toward said exhaust port;
    a liquid ejection nozzle provided at said distal end of the handpiece adjacent said aspiration needle for supplying the irrigating liquid along said aspiration needle;
    liquid passage means for supplying the irrigating liquid under pressure from said liquid inlet to said ejection nozzle; and
    valve means for directing the compressed air to flow in the reverse direction through said suction passage toward said aspiration needle to permit backwashing of the aspiration needle.

2. An endodontic irrigating instrument as defined in claim 1, wherein said valve means comprises: a valve cylinder aligned with said exhaust port of said suction pump, said valve cylinder having an inlet port communicating with said air passage; a hollow movable spool forming said air nozzle of said suction pump and defining a circumferential annular space communicating with said inlet port in said valve cylinder, said movable spool having an inlet port communicating said annular space with the internal passage of said air nozzle, said movable spool being received slidably within said valve cylinder from a first position in which said air nozzle is away from said exhaust port to a second position in which said annular space of said movable spool is in open communication with said zone of partial vacuum in said pump and in which said air nozzle closes said exhaust port, said movable spool being normally biased toward said first position; and means including a push rod for opening and closing said inlet port of said movable spool.

3. An endodontic irrigating instrument as defined in claim 2, wherein said air nozzle and said exhaust port extend substantially parallel to the longitudinal general axis of the handpiece in the direction from said distal end to said proximal end.

4. An endodontic irrigating instrument as defined in claim 1, wherein said aspiration needle is mounted to said distal end of the handpiece through a suction tube.

5. An endodontic irrigating instrument as defined in claim 4, wherein said aspiration needle is made from a flexible material.

6. An endodontic irrigating instrument as defined in claim 5, wherein said aspiration needle is made from a transparent material.

7. An endodontic irrigating instrument as defined in claim 6, wherein said material is polypropylene.

8. An endodontic irrigating instrument as defined in claim 6, wherein said material is polyethylene.

9. An endodontic irrigating instrument as defined in claim 4, wherein said suction tube extends at an angle with respect to the longitudinal general axis of the handpiece.

10. An endodontic irrigating instrument as defined in claim 1, wherein said handpiece comprises a first section including said proximal end and a second section including said distal end, said second section being mounted to said first section for swivelling movement with respect to said first section about the longitudinal general axis of the handpiece so that said aspiration needle is turned at any desired rotational angle with respect to said first section.

11. An endodontic irrigating instrument as defined in claim 1, further comprising means for regulating the flow rate of the irrigating liquid flowing through said liquid passage.

12. An endodontic irrigating instrument for irrigating a root canal of a tooth, which comprises:

a handpiece having a proximal end and a distal end, said proximal end having an inlet for a compressed air and an inlet for an irrigating liquid under pressure and being so formed as to be coupled with a multiple-channel hose extending from a dental unit;

a suction pump of the airjet type incorporated with said handpiece at the region adjacent said proximal end thereof, said suction pump having an air nozzle and and exhaust port;

air passage means for supplying a flow of compressed air from said air inlet to said nozzle to create a zone of partial vacuum in said pump;

a hollow aspiration needle mounted at an end thereof to said distal end of the handpiece, the other end thereof having an outer diameter substantially smaller than the inner diameter of the root canal to be irrigated;

suction passage means for connecting said zone of partial vacuum with said aspiration needle to suck the irrigating liquid therein and to discharge it toward said exhaust port;

a liquid ejection nozzle provided at said distal end of the handpiece adjacent said aspiration needle for supplying the irrigating liquid along said aspiration needle;

liquid passage means for supplying the irrigating liquid under pressure from said liquid inlet to said ejection nozzle; and valve means for directing the compressed air to flow in the reverse direction through said suction passage toward said aspiration needle to permit backwashing of the aspiration needle, said valve meaning including a valve cylinder aligned with said exhaust port of said suction pump, said valve cylinder having an inlet port communicating with said air passage; a hollow movable spool forming said air nozzle of said suction pump and defining a circumferential annular space communicating with said inlet port in said valve cylinder, said movable spool having an inlet port communicating said annular space with the internal passage of said air nozzle, said movable spool being received slidably within said valve cylinder from a first position in which said air nozzle is away from said exhaust port to a second position in which annular space of said movable spool is in open communication with said zone of partial vacuum in said pump and in which said air nozzle closes said exhaust port, said movable spool being normally biased toward said first position; and means including a push rod for opening and closing said inlet port of said movable spool.

* * * * *